US005733339A

United States Patent [19]
Girardot et al.

[11] Patent Number: 5,733,339
[45] Date of Patent: *Mar. 31, 1998

[54] PROCESS FOR FIXATION OF CALCIFICATION-RESISTANT BIOLOGICAL TISSUE

[75] Inventors: Jean-Marie Girardot; Marie-Nadia Girardot, both of Dunwoody, Ga.

[73] Assignee: Biomedical Design, Inc., Atlanta, Ga.

[*] Notice: The term of this patent shall not extend beyond the expiration date of Pat. No. 5,447,536.

[21] Appl. No.: 693,076

[22] PCT Filed: Feb. 16, 1995

[86] PCT No.: PCT/US95/02077

§ 371 Date: Sep. 24, 1996

§ 102(e) Date: Sep. 24, 1996

[87] PCT Pub. No.: WO95/22361

PCT Pub. Date: Aug. 24, 1995

Related U.S. Application Data

[63] Continuation-in-part of Ser. No. 195,145, Feb. 17, 1994, Pat. No. 5,447,536.

[51] Int. Cl.⁶ .................................................. A61F 2/02
[52] U.S. Cl. ........................ 8/94.11; 8/94.33; 530/356; 623/1; 623/2; 623/3; 623/11; 623/12; 523/113
[58] Field of Search ........................ 8/94.11, 94.1 R, 8/94.33, 94.12, 94.18, 94.19 C; 530/356; 623/1, 2, 3, 11, 12, 66; 427/2; 523/113

[56] References Cited

U.S. PATENT DOCUMENTS

| 4,383,832 | 5/1983 | Fraefel et al. ............................ 8/94.11 |
| 5,104,405 | 4/1992 | Nimni ........................................ 623/2 |
| 5,118,791 | 6/1992 | Burnier et al. .......................... 530/326 |
| 5,447,536 | 9/1995 | Girardot et al. ......................... 8/94.11 |

FOREIGN PATENT DOCUMENTS

| A-0037381 | 10/1981 | European Pat. Off. . |
| A-0267434 | 5/1988 | European Pat. Off. . |
| A-0401199 | 12/1990 | European Pat. Off. . |

*Primary Examiner*—Alan Diamond
*Attorney, Agent, or Firm*—Fitch, Even, Tabin & Flannery

[57] ABSTRACT

A process is provided for non-glutaraldehyde fixation of an organ or prosthesis to be implanted in a mammal. The process produces stable fixation of the tissue by forming amide linkages within and between the molecules of the tissue and employs a coupling agent, such as EDC, in combination with a coupling enhancer, such as Sulfo-NHS; diamine and/or dicarboxyl cross-linking agents are optionally included. In addition to fixing the tissue, the process prevents or retards calcification and results in a nontoxic product that does not cause inflammation.

19 Claims, No Drawings

PROCESS FOR FIXATION OF CALCIFICATION-RESISTANT BIOLOGICAL TISSUE

This application is a 371 of PCT/US95/02077 filed Feb. 15, 1995 and a continuation-in-part of our earlier U.S. application Ser. No. 08/198,145, filed Feb. 17, 1094, now U.S. Pat. No. 5,447,536 the disclosure of which is incorporated herein by reference.

The present invention relates to a process for fixing human or animal tissue prior to implantation into humans or animals, and more particularly to a fixation process that forms links within and between the proteinaceous molecules of the tissue by covalently binding the reactive amine groups and/or the reactive carboxyl groups on the tissue either directly in the presence of a coupling agent and preferably of a coupling enhancer, or through bridges formed by one or more cross-linking agent(s) in the presence of a coupling agent and preferably of a coupling enhancer.

BACKGROUND OF THE INVENTION

The surgical implantation of prosthetic devices (prostheses) into humans and other animals has been carried out with increasing frequency. Such prostheses include, by way of illustration only, heart valves, vascular grafts, urinary bladders, left ventricular-assist devices, hips, breast implants, tendons, and the like. The prosthesis can be entirely or partially made of biological tissue(s) from humans or from animals. To prevent degeneration and/or foreign body reactions, the bioprosthetic tissue must be stabilized before implantation in a human or in an animal. The stabilization process, known by those skilled in the art as fixation, consists of blocking the reactive moieties of the tissue. After it was found in 1968 that collagen, a major component of bioprostheses, was stabilized by aldehydes [Nimni et al., *J. Biol. Chem.*, 243:1457–1466 (1968)], that, of various aldehydes tested, glutaraldehyde best retarded degeneration of implanted heart valves, and that glutaraldehyde-fixed heart valves were minimally thrombogenic and had excellent biophysical and hemodynamic properties [Strawich, et al., *Biomat. Med. Dev. Art. Org.*, 3:309–318 (1975)], the process of glutaraldehyde-fixation has been and continues to be applied to most varieties of experimental and clinical bioprostheses. This process of fixation with glutaraldehyde consists of blocking the reactive amines of the tissue through formation of an aldehyde-amine bond known by the skilled in the art as a Schiff-base.

Of all glutaraldehyde-fixed bioprostheses, the heart valve has been one of the most widely studied, and its clinical application and pathology are well documented [Schoen et al., *Cardiovascular Pathology*, 1:29–52 (1992)]. Heart valve bioprostheses are generally fabricated either from glutaraldehyde-fixed porcine aortic or pulmonic valves or from glutaraldehyde-fixed bovine pericardium, which may be sewn, although not necessarily, onto a cloth-covered metallic or polymeric stent and sewing ring. These bioprostheses may be preferred over the mechanical heart valve prostheses (which typically are composed of rigid materials such as polymers, pyrocarbons and metals, and employ one or more occluders which respond passively with changes in intracardial pressure or flow) because of certain significant clinical advantages. For example, heart valve bioprostheses do not require permanent anticoagulation therapy, while mechanical heart valves do. Also, should a bioprosthesis fail, it typically first exhibits a gradual deterioration which can extend over a period of months, or even years, while a mechanical heart valve may occasionally undergo catastrophic failure. On the other hand, glutaraldehyde-fixed heart valve bioprostheses are generally less durable than mechanical heart valves mostly because they calcify.

Calcification has been recognized for more than 20 years as the main cause of failure of most bioprostheses. For example, more than 50 percent of heart valve bioprostheses fail within 10 years of implantation because of the cuspal tears and stenosis that result from calcification, which failure occurs substantially more rapidly in children than in adults [Schoen et al., *Cardiovascular Pathology*, 1:29–52 (1992)]. Although the pathogenesis of heart valve calcification (which involves not only the donor tissue, but also host factors such as blood components, and the stress to which the valve is submitted when implanted) is as yet not completely understood, glutaraldehyde has been identified as an important contributory factor [Gong, et al., *Eur J. Cardio-Thorac. Surg.* 5:288–293 (1991)]. Multiple approaches to eradicate calcification of glutaraldehyde-fixed bioprostheses have been taken.

The techniques resulting from these efforts may be broadly divided into two categories: those involving the treatment of glutaraldehyde-fixed tissue with compounds that prevent calcification, and those involving the fixation of tissue with processes that do not induce calcification. The former category of techniques includes, but is not limited to, treatment with anticalcification compounds, such as detergents or surfactants, diphosphonates, amino acids such as glutamic acid, amino-substituted aliphatic carboxylic acids such as AOA, sulfated polysaccharides, trivalent cations such as salts of iron or aluminum, elastomeric polymers, and solutions of phosphate esters, quaternary ammonium salts or sulfated aliphatic alcohols [Schoen et al, *Cardiovascular Pathology*, 1:29–52 (1992); Girardot et al., *International Journal of Artificial Organs*, 17:127–133 (1994)]. The latter category of techniques includes, but is not limited to, fixation by photo-oxidation [Moore, et al., *J. Biomed. Mater. Res.*, 28:611–618 (1994)], by treatment with polyglycidal ethers [Imamura, et al., *Jpn. J. Artif. Organs*, 17:1101–1103 (1988)]or with acyl-azide [Petite, et al., *J. Biomed. Mater. Res.*, 24:179–187 (1990)].

Because of the high incidence of calcification-induced heart valve failure and the severe clinical implications associated with this type of failure, which include reoperation, most studies on glutaraldehyde-fixed heart valves have been devoted to the pathogenesis of calcification. However, other problems have been more recently identified, which may also decrease the durability of glutaraldehyde-fixed bioprostheses. These additional problems are mostly due to the relative unstability of the Schiff-base formed between the aldehyde and the amine of the tissue and the subsequent slow release of toxic glutaraldehyde from the tissue. They include low-grade cytotoxic effects which prevent, for example, the covering of the implanted bioprosthetic tissue by antithrombogenic endothelial cells, low-grade immunological reaction by the host and slow degeneration of the bioprosthesis. Although less drastic than calcification-induced failure, this complex glutaraldehyde-related symptomatology is clinically important, and it can be fully eradicated only if the fixation method does not include glutaraldehyde.

It is therefore an object of this invention to provide a fixation method that does not utilize glutaraldehyde, which method is suitable for bioprosthetic tissues to be implanted in humans or in animals.

It is a further object of this invention to provide a fixation process for biological tissues to be used in bioprostheses, which process results in stable fixation of the tissue by forming amide linkages within and between the molecules of the tissue.

It is also an object of this invention to provide a fixation process for biological tissues that results in tissues which resist calcification, thus increasing the durability of the bioprosthesis when implanted in humans or in animals.

It is yet another object of the invention to provide a fixation process for bioprosthetic tissues that results in tissues which are biocompatible and do not induce inflammatory responses or toxic reactions when implanted in humans or in animals.

SUMMARY OF THE INVENTION

The fixation process described herein is a cross-linking process that relies on the availability of free reactive carboxyl and free reactive amine moieties on the proteins contained on and within the bioprosthetic tissue, which moieties are capable of being linked together through stable covalent amide bonds in the presence of a coupling agent, preferably with a coupling enhancer, either directly or through bridges formed by amine and/or carboxyl containing cross-linking agent(s).

In one embodiment, the coupling agent, preferably with a coupling enhancer, is used in the absence of cross-linking agents to promote amide binding between reactive carboxyl moieties and reactive amine moieties existing on the tissue. This embodiment should provide adequate fixation for tissues where reactive amines and reactive carboxyls are present on such tissues in locations close enough to be directly linked together without any intermediary cross-linking agent.

Where the reactive amine and the reactive carboxyl moieties are too distant to be attached directly to each other, adequate cross-linking of tissues is attained through cross-linking agents. One such preferred embodiment uses a coupling agent, preferably with a coupling enhancer, in the presence of one or more cross-linking agent(s). When a plurality of cross-linking agents are used, bridges of various lengths are formed by covalently binding agents to each other, with the extremities of the bridges being attached to the tissue. In this preferred embodiment, reactive moieties located close to each other on the tissue may also bind directly.

The particular desired physical properties of the bioprosthetic tissue may also determine which embodiment is employed because the length of the links between the molecules of the tissue will have an effect on the physical properties of the resultant bioprosthetic tissue. For example, for heart valve bioprostheses, where hemodynamic function is related to the flexibility of the leaflets, a cross-linking process that produces leaflets that are soft and pliable is preferred over one which produces more rigid leaflets.

The amide bonds formed with this process are more stable than the Schiff-bases formed with the glutaraldehyde process commonly used to fix biological tissues, and the resultant tissue is as cross-linked and more resistant to calcification than glutaraldehyde-fixed bioprosthetic tissue. In addition, it is not toxic, biocompatible, and does not induce inflammatory responses by the host. The proposed process thus provides tissues that are at least as suitable for implantation in humans or in animals as, and more durable than, glutaraldehyde-fixed tissues.

As used herein, the term "bioprosthetic tissue" is meant to include any organ or tissue which is derived in whole or in part from a human or an animal, or which is made from other organic tissue, and which is to be implanted by itself or as part of a bioprosthesis, in a human or in an animal. Thus, the term generally includes bioprosthetic tissue such as hearts, heart valves and other heart components, pericardium, vascular grafts, urinary tract and bladder components, tendons, bowel, soft tissues in general, such as skin, collagen and the like. Although the prosthetic tissue will very often be one which is made from natural tissues, including but not limited to bovine, ovine, porcine and possibly even human tissue, other natural materials, well known to those having ordinary skill in this art, also can be used.

The fixation method described herein consists of stabilizing the bioprosthetic tissue by binding a reactive amine or carboxyl moiety of the tissue either to another reactive moiety (carboxyl or amine) on the tissue or to one on a cross-linking agent, in such a manner as to leave few or no active moieties on or within the tissue.

The term "cross-linking", as used herein, refers to the fixation of bioprosthetic tissue that results from the formation of links of various lengths within and between the molecules of the tissue, such links resulting from amide bond formation either (a) between two reactive moieties of the tissue, thus forming short links within and between the molecules of the tissue, or (b) between reactive moieties on the tissue and each of the respective extremities of bridges formed by one or more covalently bound cross-linking agent(s), thus forming longer links within and between the molecules of the tissue.

The term "cross-linking agent", as used herein, describes a compound containing at each of its extremities free active amines and/or free active carboxyls, which moieties are capable of forming amide bonds with free active moieties that are located either on other cross-linking agent(s), thus forming chains of one or more cross-linking agent(s) either on or within the tissue, and thereby linking the free active moieties of the tissue by attachment to an extremity of such a cross-linking chain.

One or more cross-linking agents may be used, and preferably, at least two different agents are used. Each cross-linking agent has at least two reactive moieties which are preferably either carboxyls only or amines only. It is preferably a straight-chained or branched compound from about 4 to about 24 atoms in length, and most preferably from about 6 to about 8 atoms in length, with preferably one reactive moiety located at each extremity, but it can also be a cyclic compound, with the reactive moieties appropriately located on the ring. When acyclic, difunctional compounds are used, the reactive moieties are preferably separated by at least 4 carbon atoms and more preferably by at least about 6 carbon atoms. Each cross-linking agent may also be appropriately substituted, if desired. They are preferably straight chain alkanes having the reactive moieties at each extremity of the chain, and preferred cross-linking agents include, but are not limited to, suberic acid, adipic acid, terephthalic acid, 1,3,5-benzene tricarboxylic acid, 1,6-hexane diamine, 1,7-heptane diamine, triaminobenzoic acid and 2,4,6-triaminobenzene.

The concentration of each cross-linking agent can vary and depends on its efficacy to form amide bonds with the bioprosthesis and with the other cross-linking agent(s) used for fixation. In certain preferred embodiments, concentrations ranging from about 5 mM (millimolar) to about 20 mM are used; however, one skilled in the art can readily determine the appropriate concentration for each cross-linking agent.

The terms "coupling agent" and "coupling enhancer", as used herein, refer to reagents that respectively promote and enhance the formation of amide bonds. These bonds may be formed between a reactive amine and a reactive carboxyl on the tissue (thus linking two such closely located reactive groups), between a reactive amine on one cross-linking agent and a reactive carboxyl on another cross-linking agent (thus forming chains of various lengths between cross-linking agents), and between two reactive amines or carboxyls located at the extremities of such a cross-linking bridge and the reactive carboxyl or amine moieties located on and within the tissue (thus forming links of various lengths within and between the molecules of the bioprosthetic tissue). Those of skill in the peptide synthesis and related art will be familiar with such reagents, e.g. water-soluble carbodiimides and succinimides.

The coupling agent used in the preferred embodiments is 1-ethyl-3(3-dimethyl aminopropyl)carbodiimide hydrochloride (EDC), although other suitable coupling agents such as N-hydroxysuccinimide can also be used. The coupling enhancer used in the embodiment where EDC is used as the coupling agent is N-hydroxysulfosuccinimide (sulfo-NHS), although other suitable coupling enhancers can also be used. The concentration of the coupling agent and of the coupling enhancer can vary. However, appropriate concentrations are readily determinable by those of skill in the art. Preferably, the coupling agent is used in a concentration between about 10 mM and 500 mM and more preferably at about 100 mM or less. The coupling enhancer is preferably employed at between 0.5 mM and about 50 mM and more preferably at about 10 mM or less.

The cross-linking agents, the coupling agent and the coupling enhancer as well as their reaction products should be preferably water-soluble. They should be selected to be such as to maximize fixation and optimizing cross-linking of the tissue while minimizing the risks of damage to the prosthetic tissue during the fixation process, and of toxicity, inflammation, calcification, etc, after implantation. All solutions used for cross-linking are preferably filtered before use through 0.45 μm or less filters to minimize risks of contamination.

Reaction conditions for the cross-linking of the prosthesis may vary, depending on the cross-linking, coupling and enhancing agents employed. In general, the cross-linking process is carried out in an aqueous buffer selected from among those well known to those of ordinary skill in this art as to provide the most efficacious cross-linking reaction, while minimizing risks of calcification. Examples of suitable buffers include, but are not limited to, N-2-hydroxyethylpiperazine-N'-ethanesulfonic acid (HEPES) and 3-(N-morpholino)propanesulfonic acid (MOPS), and the like.

The pH and concentration of the buffered solution also can vary, again depending upon the cross-linking, coupling and enhancing agents employed. In preferred embodiments, the buffer concentration and pH are chosen to provide the most effective cross-linking reaction while being the least harmful to the prosthesis. For example, with EDC as the coupling agent and sulfo-NHS as the coupling enhancer, the pH of the cross-linking reaction is about 6.0 to about 7.4. The temperature of the reaction is maintained between about 40° C. and 0° C.; preferably, the reaction is carried out between 21° and 25° C.

Typically, the fresh prosthetic tissue to be fixed by the cross-linking method described in the present invention is kept on ice until it is rinsed several times in ice-cold 0.85% saline or other solutions known by those of skill in the art, preferably immediately after and no longer than 48 hours after being excised from the donor animal. If additional storage time is needed, the rinsed tissue is then stored, but not longer than 24 hours, in an appropriate buffer as described further below, at a low temperature, such as about 4° C.

The bioprosthetic tissue is then cross-linked in one or more consecutive steps by incubation in the presence of a coupling agent, preferably with a coupling enhancer, either in the presence or in the absence of one or more cross-linking agents. When more than one cross-linking agent is used together with the coupling and enhancing agents, they can be used either in a single step or, preferably, sequentially in several consecutive steps.

In a preferred embodiment where a dicarboxylic acid and a diamine are used as cross-linking agents, the two agents are used alternately in a three-step process. As such, either the dicarboxylic acid or the diamine is used in the first step, the alternate agent is used in the second step, and the first agent is used again in the third step. At the end of this cross-linking process, the free active moieties of the tissue are either linked together directly, or they are connected together through bridges composed of between 1 and 5 links alternating between the dicarboxylic acid and the diamine. For illustration, in the preferred embodiment where the diamine is used during the first and third steps, and the diacid is used during the second step, the one-link bridges result from attachment of each of two reactive amines of a diamine, or each of two reactive carboxyls of a diacid to, respectively, two reactive carboxyl moieties or two reactive amine moieties on the tissue; the five-link bridges result from anchoring one reactive amine from each of two diamine molecules to a reactive carboxyl on the tissue, the other amine of each of the two molecules remaining free for further reaction (first step). Each of the two free amines then binds to one reactive carboxyl group on two different diacid molecules, leaving one carboxyl group on each of the two diacid molecules free for further reaction (second step). Finally, each of the two free reactive carboxyl moieties on the diacid molecules binds to a reactive amine of a diamine molecule (third step), thus forming the 5-link bridge between two moieties on the tissue.

For each step of the cross-linking process, the time of incubation generally depends upon the nature and concentration of the cross-linking, coupling and enhancer agents used, and upon the cross-linking conditions, such as pH and temperature. For instance, an incubation time for each step from about 3 hours to about 48 hours is preferably employed when EDC and sulfo-NHS are used as the coupling and enhancer agents, respectively. After each step, the tissue is rinsed or washed in aqueous buffer to remove the non-reacted reagents and their by-products. At the end of the cross-linking process, the tissue is kept until further use in a sterile buffered solution. Appropriate rinsing and buffer solutions are used as previously described and as understood by those of skill in this art.

The present invention is further described by the examples that follow. Because different bioprosthetic tissues prefer different types of cross-links depending on the nature of their structure and of their intended use, the examples describe cross-linking processes that vary in terms of the presence or absence of cross-linking agents, of the types of cross-linking agents, and of the number of steps, thus resulting in cross-links that vary in either their nature and/or their complexity. The examples are not to be construed as limiting in any way either the spirit or the scope of the present invention.

The coupling agent used in the examples is 1-ethyl-3(3-dimethyl aminopropyl) carbodiimide hydrochloride (EDC), and the coupling enhancer is N-hydroxy-sulfosuccinimide (sulfo-NHS). They are commercially available from Sigma and Pierce. The cross-linking agents are 1,6-hexane-diamine (DIA), a C-6 straight-chain aliphatic agent with an amine group at each end of the chain, and suberic acid (SUA), a C-8 straight-chain aliphatic agent with a carboxyl group at each end of the chain, or 1,3,5-benzenetricarboxylic acid (BCA), an agent with 3 reactive carboxyl groups on the benzene ring, are readily obtainable from Aldrich. All agents are solubilized in 10 mMHEPES buffer containing 0.85% of sodium chloride, pH 6.5 (HEPES buffer). Their concentrations are expressed as mM (number of millimoles of chemical for each liter of solution), or as % (grams per 100 ml of solution). The temperatures are in ° C. (degrees Celsius).

EXAMPLE 1

A process embodying one feature of the present invention is illustrated by the use of EDC and sulfo-NHS in the absence of any cross-linking agent, thus cross-linking the biological tissue by forming only short links between free active carboxyls and free amines that are located close to each other on the tissue.

1. Preparation of heart valve tissue

Leaflets and 1×1 cm aortic wall coupons were dissected from fresh porcine hearts kept on ice. The samples were then rinsed 6 times for 5 minutes each time in ice-cold saline to remove red blood cells and other debris, and stored overnight at 4° C. in HEPES buffer, pH 6.5. The samples used for Examples 1–4 were randomly selected from this original pool. Samples to be used as "fresh" controls, also selected from this pool, were kept until testing at 4° C. in HEPES buffer containing 20% of isopropanol. In addition, leaflets and wall coupons dissected from glutaraldehyde-fixed valves provided by the Heart Valve Division of Medtronic, Inc., also kept at 4° C. in HEPES buffer containing 20% of isopropanol, represented the "standard" control condition.

2. Cross-linking of porcine aortic valve

Samples randomly selected from the original pool were incubated three times for 48 hours at room temperature in HEPES buffer containing 50 mM of EDC and 2.5 mM of sulfo-NHS, thus forming short links directly between free active carboxyl and amines of the tissue. At the end of the cross-linking process, the samples were placed in HEPES buffer containing 20% of isopropanol.

EXAMPLE 2

Fixation is carried out employing a 3-step cross-linking process that uses EDC and sulfo-NHS in the presence of SUA in the first step, DIA in the second step, and SUA again in the third step. Samples randomly selected from the original pool described in Example 1 were cross-linked and stored as in Example 1, except that 10 mM SUA, 15 mM DIA and 10 mM SUA were added to EDC and sulfo-NHS during the first, second and third steps of the cross-linking reactions, respectively. As a result, there are formed the following types of links of various lengths between the free active moieties of the tissue: direct links, one-link bridges made of either SUA or DIA, two-link bridges made of the two cross-linking agents covalently bound to each other, three-link bridges made of chains formed by one molecule of SUA, one molecule of DIA, and one molecule of SUA covalently bound together, four-link bridges composed as the three-link chains with further addition of one molecule of DIA, and five-link bridges composed as the four-link bridges with further addition of one molecule of SUA. The two extremities of each bridge are connected via amide bonds with one free moiety on the tissue.

EXAMPLE 3

A 3-step cross-linking process is employed that is similar to the process used in Example 2, but which reverses the order of cross-linking agents used in the three sequential steps. As such, 15 mM DIA was used in the first step, 10 mM SUA in the second step, and 15 mM DIA again in the third step, thus forming direct links, one-link bridges made of either DIA or SUA with each of the two ends covalently bound respectively to an amine or a carboxyl group on the tissue, and two-, three-, four- and five-link bridges formed respectively by chains of DIA-SUA, DIA-SUA-DIA, DIA-SUA-DIA-SUA, and DIA-SUA-DIA-SUA-DIA molecules covalently bound to each other, with the two extremities of each bridge forming amine bonds with free moieties on the tissues.

EXAMPLE 4

A 3-step cross-linking process is employed that is similar to the process used in Example 2, but which uses BCA instead of SUA. As such, 7 mM BCA was used in the first step, 15 mM DIA in the second step, and 7 mM BCA again in the third step. Because BCA has three carboxyls located on a benzene ring, the cross-links formed by this process are generally more complex than the linear bridges obtained when the cross-linking agent includes an aliphatic chain, such as SUA.

EXAMPLE 5

A cross-linking process is carried out in only two steps, where EDC and sulfo-NHS are used in the presence of DIA in the first step and of SUA in the second step. As a result, three types of links are formed between the free active moieties of the tissue: direct links, one-link bridges made of either SUA or DIA, with the two ends of each bridge binding to two amines or to two carboxyls of the tissue, respectively, and two-link bridges made of the two cross-linking agents covalently bound to each other, with one end binding to a free amine of the tissue, and the other end binding to a free carboxyl group of the tissue.

Fresh porcine valves were incubated first for 48 hours in HEPES buffer containing 15 mM DIA, and then for 48 hours in HEPES buffer containing 10 mM SUA, with 20 mM EDC and 1 mM sulfo-NHS added at each step, with the valves being rinsed three times with HEPES buffer between the first and second steps. At the end of the process, cusps and 1×1 wall coupons were dissected from the fixed valves, and stored at room temperature in HEPES buffer containing 20% of isopropanol, pH 7.4. Fresh and glutaraldehyde controls were prepared as described in Example 1.

EXAMPLE 6

An alternative, single step, cross-linking process that uses EDC and sulfo-NHS in the presence of, simultaneously, both cross-linking agents DIA and SUA, thus forming a more complex network of cross-links, i.e. the types of links and bridges as described in Example 2 and in Example 3 above.

Fresh porcine aortic valves were incubated at 4° C. in 200 ml per valve of HEPES buffer containing 15 mM of DIA and 10 mM of SUA. After 24 hours, the valves were drained and kept at room temperature for 72 hours in a solution of 20 mM EDC and 1 mM sulfo-NHS in HEPES buffer. At the end of the process, cusps and 1×1 wall coupons were dissected from the fixed valves, and stored at room temperature in HEPES buffer containing 20% of isopropanol, pH 7.4. Glutaraldehyde controls were prepared as described in Example 1.

CHARACTERIZATION OF CROSS-LINKED PORCINE AORTIC VALVES

The porcine aortic valve tissues fixed as described in Examples 1 to 6, inclusive, were subjected to a variety of tests well known to those skilled in the art, which determine the degree to which bioprosthetic tissues are fixed and cross-linked, and to which they resist calcification. The cross-linked tissues were also submitted to histology and biocompatibility studies. Appropriate fresh and glutaraldehyde-fixed samples, that were prepared and stored as described in Examples 1 to 6, were used as controls.

1. DENATURATION TEMPERATURE

This test is used to evaluate the stability of the cross-linked triple helical structure of collagen, a major constituent of many bioprosthetic tissues, and it consists of recording the temperature at which a sample starts shrinking when immersed in distilled water placed over a heat source, this temperature being known to those skilled in the art as the shrink temperature or denaturation temperature. The shrink temperature increases as a function of collagen cross-linking. Typically, a sample is immersed in distilled water at 45° C. The temperature of the water is then raised at a rate of 1.5° C. per minute until the sample starts shrinking, at which time the temperature is recorded as the denaturation temperature. The results of this test, based on 3 leaflets from Examples 1-6 and the appropriate controls, are reported in Table 1 and demonstrate that the shrink temperatures are significantly higher for all fixed leaflets than for the fresh leaflets, with the shrink temperatures for Examples 1 to 6 at least as high as for the glutaraldehyde controls, thus indicating that the collagen cross-linked as described in Examples 1 to 6 is at least as stable as the collagen cross-linked with the standard glutaraldehyde fixation process.

TABLE 1

| EXAMPLES | CROSS-LINKING AGENTS | | | SHRINK TEMPERATURE |
|---|---|---|---|---|
| | Step 1 | Step 2 | Step 3 | Mean ± SEM °C. |
| 1 | none | none | none | 86.5 ± 0.2* |
| 2 | SUA | DIA | SUA | 88.4 ± 0.2* |
| 3 | DIA | SUA | DIA | 90.7 ± 0.1* |
| 4 | BCA | DIA | BCA | 88.8 ± 0.0* |
| Fresh | | | | 70.3 ± 0.1 |
| Glutaraldehyde-fixed | | | | 85.4 ± 0.1* |
| 5 | SUA | DIA | — | 87.1 ± 0.1* |
| Fresh | | | | 66.5 ± 0.3 |
| Glutaraldehyde-fixed | | | | 86.3 ± 0.2* |
| 6 | DIA + SUA | — | — | 87.4 ± 0.3 |
| Glutaraldehyde-fixed | | | | 86.5 ± 0.2 |

*significantly higher than fresh controls, p < 0.05 (Newman-Keuls test)

2. RESIDUAL AMINE TEST

This test evaluates the stability of the cross-linked tissue by determining the number of amine groups that remain free in the bioprosthetic tissue at the end of the cross-linking process. It consists of incubating the cross-linked sample in a ninhydrin solution, which alters its coloration in the presence of free amines. Typically, the samples are individually incubated at 95° C. for 20 minutes in 1 ml of ninhydrin in citrate buffer, pH 5.0, dried and weighed. Each incubation solution is then diluted with 1 ml of 50% isopropanol in distilled water, and its optical density, which is read at 570 nm using a spectrophotometer, is applied to a standard linear equation determined by using various concentrations of 1-norleucine, and divided by the dry weight of the sample, thus providing a value of residual amines expressed as nanomoles of amines per mg of dry tissue. The results, obtained from 3 leaflets and 3 wall coupons from each of Examples 1 to 4, are reported in Table 2.

TABLE 2

| | CROSS-LINKING AGENTS | | | RESIDUAL AMINES nmoles/mg dry tissue | |
|---|---|---|---|---|---|
| | Step | Step | Step | Mean ± SEM | |
| EXAMPLES | 1 | 2 | 3 | Leaflets | Walls |
| 1 | none | none | none | 50.7 ± 3.3* | 30.3 ± 0.7* |
| 2 | SUA | DIA | SUA | 11.0 ± 0.0* | 15.0 ± 1.5* |
| 3 | DIA | SUA | DIA | 35.3 ± 1.8* | 24.7 ± 0.7* |
| 4 | BCA | DIA | BCA | 18.7 ± 1.8* | 19.7 ± 0.9* |
| Fresh | | | | 136.0 ± 2.0 | 83.0 ± 7.4 |
| Glutaraldehyde-fixed | | | | 9.3 ± 0.7* | 3.7 ± 0.3* |

*Significantly lower than Fresh controls, p < 0.05 (Newman-Keuls test).

Although a proportion of the free amines expressed for Examples 2 to 4 may be explained by unreacted amines of DIA molecules that were anchored by one extremity only, the tissue cross-linked as in Examples 1 to 4 contained significantly less amines than the Fresh controls. In addition, significantly more amines remained free when the leaflets and the walls were fixed in the absence of (Example 1), rather than in the presence of cross-linking agents (Examples 2 to 4), probably because the relative spatial isolation of many reactive tissue amines permitted connection to carboxyls on the tissue only by bridges formed by the cross-linking agents. Thus, although fixation in the absence of cross-linking agents, as described in Example 1, may be adequate for tissues where many free amines are close enough to reactive carboxyls to permit direct amide linking in the presence of a coupling agent, some bioprosthetic tissues, e.g. heart valves, are preferably stabilized in the presence of one or more cross-linking agent(s).

3. TEST OF RESISTANCE TO COLLAGENASE

This test determines the degree of fixation of bioprosthetic tissues by evaluating their resistance to digestion by collagenase, a proteolytic enzyme specific for collagen, and consists of determining the amount of amines that are released from tissue when it is incubated in a solution containing collagenase. Resistance to collagenase digestion for 3 leaflets and 3 pieces of walls, cross-linked as in Examples 1-6 (with their appropriate fresh and glutaraldehyde-fixed controls), was tested by mincing and then incubating each sample at 37° C. for 27 hours in 3 ml of a solution containing 5 mg of collagenase, 180 mg of $CaCl_2 \cdot 2H_2O$ in HEPES buffer, pH 7.4. The level of amines in each sample was determined by the ninhydrin test previously described (refer to residual amines test), using 0.1 ml of collagenase solution in 1 ml of ninhydrin solution.

The results, which are reported in Table 3, clearly demonstrate that the level of amines released in the collagenase solution is significantly lower for all fixed leaflets and walls than for the Fresh controls, thus indicating that all bioprosthetic tissues prepared as described in Examples 1-6 strongly resist collagenase digestion and are well fixed.

TABLE 3

| EXAMPLES | CROSS-LINKING AGENTS | | | AMINES RELEASED Mean ± SEM nmoles/mg | |
|---|---|---|---|---|---|
| | Step 1 | Step 2 | Step 3 | Leaflets | Walls |
| 1 | none | none | none | 5.5 ± 0.5* | 6.4 ± 0.1* |
| 2 | SUA | DIA | SUA | 3.9 ± 0.2* | 4.9 ± 0.1* |
| 3 | DIA | SUA | DIA | 2.9 ± 0.5* | 5.3 ± 0.4* |
| 4 | BCA | DIA | BCA | 4.5 ± 0.8* | 5.5 ± 0.3* |
| Fresh | | | | 359.2 ± 22.8 | 347.0 ± 24.0 |
| Glutaraldehyde-fixed | | | | 0.9 ± 0.1* | 1.0 ± 0.2* |
| 5 | SUA | DIA | — | 16.1 ± 0.6*# | 17.2 ± 0.5*# |
| Fresh | | | | 2260 ± 153.7# | 936.9 ± 76.3# |
| Glutaraldehyde-fixed | | | | 6.1 ± 1.0*# | 2.3 ± 0.2*# |
| 6 | DIA + SUA | — | — | 969.0 ± 7.4*# | 38.7 ± 4.2*# |
| Glutaraldehyde-fixed | | | | 9.3 ± 3.6# | 3.9 ± 3.2# |

*Significantly lower than Fresh controls, p < 0.05 (Newman-Keuls test)
The samples were incubated for 72 instead of 27 hours.

The results for Examples 1 to 6 are slightly higher than those for their respective glutaraldehyde-fixed controls. This difference is not considered to reflect differences in resistance to collagenase but instead to result from the constant release during incubation of glutaraldehyde from the glutaraldehyde-fixed samples—which then binds both to the collagenase of the solution, thus decreasing the efficacy of the collagenase solution, and also to the amines released from the tissue, thus decreasing the number of free amines.

4. TEST OF RESISTANCE TO PROTEASE

This test determines the degree of fixation of bioprosthetic tissues by evaluating their resistance to digestion by protease, a non-specific proteolytic enzyme; it typically consists of determining the weight lost by a tissue that is incubated in a solution containing protease. The test was conducted on 3 leaflets and 3 pieces of walls cross-linked as in Examples 1–6 (with their appropriate fresh and glutaraldehyde-fixed controls). The samples were blotted, weighed, incubated in 3 ml of a solution prepared by dissolving 75 mg of protease and 75 mg of $CaCl_2 \cdot H_2O$ in 150 ml of HEPES buffer, pH 7.4, blotted and weighed. The results (expressed as % of weight remaining in the tissue), which are reported in Table 4, clearly demonstrate that porcine aortic valves prepared as described in Examples 1 to 6 strongly resist non-specific degradation by protease.

TABLE 4

| EXAMPLES | CROSS-LINKING AGENTS | | | % WEIGHT REMAINING Mean ± SEM | |
|---|---|---|---|---|---|
| | Step 1 | Step 2 | Step 3 | Leaflets | Walls |
| 1 | none | none | none | 47.7 ± 0.7* | 50.6 ± 2.2* |
| 2 | SUA | DIA | SUA | 59.1 ± 1.7* | 51.8 ± 3.5* |
| 3 | DIA | SUA | DIA | 49.6 ± 2.6* | 55.8 ± 1.6* |
| 4 | BCA | DIA | BCA | 52.5 ± 3.5* | 49.5 ± 1.0* |
| Fresh | | | | 0.0 ± 0.0 | 0.8 ± 0.4 |
| Glutaraldehyde-fixed | | | | 27.2 ± 1.5* | 32.5 ± 3.2* |
| 5 | SUA | DIA | — | 64.4 ± 4.2* | 40.0 ± 0.5* |
| Fresh | | | | 0.0 ± 0.0 | 0.0 ± 0.0 |
| Glutaraldehyde-fixed | | | | 68.8 ± 4.1* | 34.1 ± 3.2* |
| 6 | DIA + SUA | — | — | 69.9 ± 1.3 | 30.4 ± 1.1 |
| Glutaraldehyde-fixed | | | | 71.5 ± 3.4 | 26.1 ± 0.4 |

*significantly higher than Fresh controls at p < 0.05 (Newman-Keuls test)

Based on the results of the denaturation temperature test, the residual amines test, and the resistance to collagenase and to protease tests, it is shown that bioprosthetic tissues cross-linked by the processes hereinbefore described which embody various features of the present invention are as well fixed and cross-linked as bioprosthetic tissues fixed with the standard glutaraldehyde process. However, because the amide bonds formed with the present invention are more stable than the Schiff-bases formed with the glutaraldehyde process, the bioprosthetic tissues resulting from use of the present invention will not induce low-grade toxic effects and undergo long-term degeneration, which is a considerable advantage over the glutaraldehyde-fixed bioprosthetic tissues.

5. TEST OF RESISTANCE TO CALCIFICATION

Another important advantage of the present invention over the standard glutaraldehyde process is illustrated by comparing the calcium levels of the tissues cross-linked as described in Examples 1–6 with those of glutaraldehyde-fixed tissues, when they are implanted subdermally in weaning rats; this is a model of calcification known as a standard screening model by those who are skilled in the art of bioprostheses.

Six leaflets and 6 wall coupons from porcine aortic valves from each of Examples 1 to 6, and their appropriate glutaraldehyde-fixed controls, were rinsed 3 times with sterile saline and implanted subdermally for 4 weeks or 8 weeks in the abdomen of 3-week old male Sprague-Dawley rats. The retrieved samples were then cleaned of surrounding tissues, lyophilized, weighed, hydrolyzed in 1 ml of ultrapure 6N HCl at 85° C. for 24 hours, and submitted to calcium determination by either Inductively Coupled Plasma analysis or by Atomic Absorption. The results (Table 5) indicate that the leaflets and the walls of Examples 1–6 were significantly less calcified than the glutaraldehyde-fixed controls and that leaflets were not significantly more calcified at 8 weeks than at 4 weeks; they thus demonstrate that porcine heart valves are more resistant to calcification when cross-linked with the processes embodying features of the present invention than when fixed by the standard glutaraldehyde process.

TABLE 5

| EXAMPLES | CROSS-LINKING AGENTS | | | CALCIUM mg/g dry sample Mean ± SEM | | |
|---|---|---|---|---|---|---|
| | Step 1 | Step 2 | Step 3 | Leaflets 4-week | 8-week | Walls 4-week |
| 1 | none | none | none | 25 ± 15* | 21 ± 19* | 40 ± 8* |
| 2 | SUA | DIA | SUA | 9 ± 5* | 31 ± 21* | 35 ± 4* |

TABLE 5-continued

| | CROSS-LINKING AGENTS | | | CALCIUM mg/g dry sample Mean ± SEM | | |
|---|---|---|---|---|---|---|
| | | | | Leaflets | | Walls |
| EXAM-PLES | Step 1 | Step 2 | Step 3 | 4-week | 8-week | 4-week |
| 3 | DIA | SUA | DIA | 8 ± 5* | 19 ± 18* | 26 ± 14* |
| 4 | BCA | DIA | BCA | 4 ± 2* | 36 ± 13* | 33 ± 5* |
| Glutar-aldehyde-fixed | | | | 204 ± 10 | 230 ± 34 | 130 ± 8 |
| 5 | SUA | DIA | | 24 ± 6 | — | 85 ± 15 |
| Glutar-aldehyde-fixed | | | | 220 ± 8 | — | 105 ± 5 |
| 6 | DIA ± SUA | — | — | 1 ± 1* | — | 43 ± 7* |
| Glutar-aldehyde-fixed | | | | 185 ± 11 | — | 65 ± 3 |

*Significantly lower than glutaraldehyde controls, p < 0.05 (Newman-Keuls test)

These results with respect to calcification in the rat model show that the high rate of failure of bioprosthetic devices, which is believed to be currently due primarily to calcification, should be considerably reduced by use of the present invention.

6. HISTOLOGY STUDIES

These studies were performed to ensure that the cross-linking processes described in the present invention do not induce deleterious effects on the structure of the bioprosthetic tissue that could adversely affect the function of the bioprosthetic tissue, and they also are effective to evaluate the "quality" of these tissues before and after implantation.

One such study was performed by viewing bioprosthetic tissues cross-linked as described in the present invention under scanning electron microscopy. Three leaflets from each of Examples 1 to 4 and from their appropriate glutaraldehyde-fixed controls were cut transversely to expose the internal layers (fibrosa, spongiosa and ventricularis). They were then critically point-dried in ethanol, coated with AuPd and examined using a Hitachi S-800 field emission scanning electron microscope at 15 KV. This study demonstrated that the leaflets from Examples 1 to 4 had normal morphology; the tissue was compact, there was no sign of delamination, and the inflow and outflow surfaces of the leaflets showed no sign of roughening.

The other histology study was performed by viewing, under light microscope, unimplanted and implanted leaflets from porcine aortic valves that have been cross-linked as described using processes embodying various features of the present invention. Three unimplanted leaflets, and three leaflets subdermally implanted in rats for 4 weeks, from each of Examples 1 to 4 and from their appropriate glutaraldehyde-fixed controls, were placed in 4% glutaraldehyde and sent to Dr. Frederick Schoen, Brigham and Women's Hospital, Boston, Mass., where they were embedded in JB-4 glycol methacrylate medium. Sections 2 to 3 µm thick were then stained for cells with hematoxylin and eosin, for calcium salts with the von Kossa stain, and for collagen, elastin and mucopolysaccharides with the Movat pentachrome stain. Although leaflets from Examples 1 (3 steps with EDC and sulfo-NHS in the absence of cross-linking agents) and 4 (3-step treatment with the cross-linking BCA used for the first and third steps instead of SUA) occasionally exhibited mild edema and moderate smudging of the fibrosa collagen, they appeared much less calcified than the glutaraldehyde-fixed leaflets. On the other hand, the leaflets treated in Examples 2 and 3 (3-step reactions with the cross-linking agents SUA/DIA/SUA and DIA/SUA/DIA, respectively) appeared to be better preserved, and to calcify considerably less, than glutaraldehyde-fixed leaflets, without exhibiting any sign of inflammatory reaction.

8. BIOCOMPATIBILITY STUDY

Twenty leaflets from Example 1 were sent to Dr. James A. Anderson at Case Western University, Cleveland, Ohio, where they were sterilized, placed in small stainless steel wire mesh cages and implanted subdermally in rats. Empty cages served as controls. The degree of inflammatory response was determined at 4, 7, 14 and 21 days of implantation by quantitative and differential measurement of leucocytes, polymorphonuclear and macrophage counts, and by alkaline and acid phosphatase analyses of the exudate that collected in the cages.

The results of these measurements and analyses demonstrated that the leaflets were found to be biocompatible and nontoxic, thus indicating that bioprosthetic tissues cross-linked by processes embodying features of the present invention are suitable for implantation.

EXAMPLE 7

The processes of Examples 2 and 3 are repeated except that, in both instances the fixation processes are halted after the first step. After draining and rinsing, the samples are stored in HEPES buffer at pH 7.4 containing 20% isopropanol at room temperature. Testing for thermal denaturation, collagenase digestion, protease digestion and resistance to calcification is carried out as reported hereinbefore, together with appropriate control samples of fresh tissue, and the resultant cross-linked materials are compared to glutaraldehyde-treated samples. The samples incubated either with a mixture of diamine, EDC and sulfo-NHS or with a mixture of suberic acid, EDC and sulfo-NHS are considered to exhibit thermal stability and resistance to protease digestion far superior to fresh tissue and as good as the glutaraldehyde-treated samples. Although the resistance to collagenase digestion may not be quite as good as glutaraldehyde-treated samples, it is considered to be fully adequate. Resistance to calcification of both such sets of cross-linked samples is considered to be superior to that of glutaraldehyde-fixed material.

Although the invention has been described with regard to a number of preferred embodiments, which constitute the best mode presently known to the inventors for carrying out this invention, it should be understood that various changes and modifications, as would be obvious to one having the ordinary skill in this art, may be made without departing from the scope of the invention which is defined by the claims that are appended hereto. For example, if the initial treatment of a 3-step process using cross-linking agents at each step is carried out using one dicarboxylic acid, and although it may be preferable to employ the same type of carboxylic acid for the third step of the reaction, a different dicarboxylic acid or a tricarboxylic acid could be alternatively employed. The foregoing similarly applies when a diamine is employed in the first treatment step. Rather than using a single solution containing both the coupling agent and the cross-linking agent, treatment may be carried out sequentially with two separate solutions. Also, although 2 or 3 steps may be preferred to provide adequate cross-linking for some tissues, other tissues may already be adequately cross-linked after a single step.

Particular features of the invention are emphasized in the claims that follow.

What is claimed is:

1. A process for fixing animal tissue to render it suitable for implantation in living mammals, comprising treating said animal tissue with an effective amount of a coupling agent which promotes the formation of amide bonds between reactive carboxy moieties and reactive amino moieties in combination with a coupling enhancer, so as to result in the formation of amidated links to reactive moieties carried by the molecules of said animal tissue to render said tissue resistant to protease digestion and to calcification.

2. The process of claim 1 wherein said tissue is also treated with a cross-linking agent containing either at least two reactive amine moieties or at least two reactive carboxy moieties.

3. The process of claim 2 wherein said cross-linking agent is a water-soluble di- or tri-amine or a water-soluble di- or tri-carboxylic acid, and said coupling agent is water-soluble.

4. The process of claim 3 wherein said cross-linking agent has a carbon chain at least 4 carbon atoms in length.

5. The process of claim 1 wherein said coupling agent is 1-ethyl-3(3-dimethyl aminopropyl) carbodiimide (EDC).

6. A prosthesis treated according to the process of claim 1 which resists calcification.

7. A prosthesis treated according to the process of claim 5 which resists calcification.

8. A process according to claim 1 comprising the steps of:

a) treating said animal tissue with a first cross-linking agent containing either at least two reactive amino groups or at least two reactive carboxyl groups, in the presence of said coupling agent, such that at least one of said reactive groups forms an amide bond with a reactive moiety on said tissue molecules while another reactive group on at least some portion of said first cross-linking agent remains free; and b) repeating the treatment described in (a) in the presence of said coupling agent with a second cross-linking agent containing at least two reactive carboxyl groups if said first cross-linking agent used in (a) contains amino groups, or vice-versa if said first cross-linking agent contains carboxyl groups, such that additional amide bonds are formed between reactive groups of said second cross-linking agent and either said free groups on said first cross-linking agent or reactive moieties on said tissue molecules, resulting in the formation of links between or within the molecules of said animal tissue wherein some of said links are chains containing at least one of both said first and second cross-linking agents.

9. The process of claim 8 wherein step (a) is repeated after step (b) using a third cross-linking agent which is the same as or equivalent to said first cross-linking agent so as to create further amide bonds (i) between one reactive group of said third cross-linking agent and a free reactive group on said second cross-linking agent and (ii) between another reactive group on said third cross-linking agent and a free reactive moiety on a tissue molecule, thereby increasing the number of said links formed between and within the molecules of said tissue.

10. The process of claim 8 wherein said first and second cross-linking agent comprise water-soluble di- or tri-amines and water-soluble di- or tri-carboxylic acids and said coupling agent is water-soluble.

11. The process of claim 8 wherein said first and second cross-linking agents are each at least 4 carbon atoms in length.

12. The process of claim 8 wherein step (a) employs 1,6 hexane diamine, and step (b) employs suberic acid or 1,3,5-benzenetricarboxylic acid.

13. The process of claim 8 wherein step (a) employs suberic acid or 1,3,5-benzenetricarboxylic acid and step (b) employs 1,6 hexane diamine.

14. A prosthesis treated according to the process of claim 8.

15. A process for fixing animal tissue to render it suitable for implantation in living mammals, which process comprises treating said animal tissue with an aqueous solution which contains a water-soluble first reagent having at least 2 reactive amine groups, and a water-soluble second reagent containing at least 2 reactive carboxyl groups, and also with a water-soluble coupling agent plus a water-soluble coupling enhancer, such that said reactive amine and carboxylic groups are promoted to form amide bonds with tissue molecules having reactive moieties thereon, and washing said treated animal tissue to remove unreacted reagents and render it suitable for implantation.

16. (Amended) A process according to claim 15 wherein said animal tissue is sequentially treated with said tissue being first contacted with a first aqueous solution containing said first and second reagents and after removal of said first solution being thereafter treated with a second aqueous solution containing said water-soluble coupling agent plus said water-soluble coupling enhancer that promotes said reactive groups to form amide bonds.

17. A process according to claim 16 wherein said second solution contains 1-ethyl-3(3-dimethyl aminopropyl) carbodiimide (EDC) and N-hydroxysulfosuccinimide (sulfo-NHS) as said water-soluble coupling agent and said water-soluble coupling enhancer.

18. A prosthesis formed at least partially of prosthetic tissue containing cross-links between and within the proteinaceous molecules of said prosthetic tissue, which cross-links are comprised of amide bonds between reactive moieties on said tissue and additional amide bonds between reactive moieties on said tissue and first and second cross-linking agents, both of which are between 4 carbon atoms and 8 carbon atoms in length and which first cross-linking agents have at least 2 reactive amino groups and which second cross-linking agents have at least 2 reactive carboxyl groups, which cross-linking of said prosthetic tissue via said amide bonds and said additional amide bonds is such that the prosthetic tissue is fixed, resists calcification and does not induce inflammatory responses upon implantation into a living mammal.

19. The prosthesis of claim 18 wherein said cross-links which include said additional amide bonds are formed of residues of said cross-linking agents which are selected from the group consisting of 1,6 hexane diamine, suberic acid and 1,3,5-benzenetri carboxylic acid.

* * * * *

UNITED STATES PATENT AND TRADEMARK OFFICE
CERTIFICATE OF CORRECTION

PATENT NO : 5,733,339
DATED     : March 31, 1998
INVENTOR(S): Girardot, et al.

It is certified that error appears in the above-identified patent and that said Letters Patent is hereby corrected as shown below:

<u>IN THE TITLE</u> Page
Section [63], "195,145" should be --198,145--.

line 7, "1094" should be --1994--.
Column 11, line 19, "969.0" should be --96.0--.

Signed and Sealed this

Twenty-ninth Day of September, 1998

Attest:

BRUCE LEHMAN

Attesting Officer

Commissioner of Patents and Trademarks